United States Patent [19]

Chon et al.

[11] Patent Number: 5,508,624
[45] Date of Patent: Apr. 16, 1996

[54] METHOD FOR MEASURING DEGRADATION LEVEL OF TRANSFORMER INSULATING OIL IN USE, AND APPARATUS FOR CARRYING OUT THE METHOD

[75] Inventors: Young K. Chon, Kyongsangnam Do; Kyung H. Ko, Pusan, both of Rep. of Korea

[73] Assignees: Korea Electrotechnology Institute, Kyongsangnam Do; Kangnam Industrial Co., Ltd., Pusan, both of Rep. of Korea

[21] Appl. No.: 301,906

[22] Filed: Sep. 7, 1994

[30] Foreign Application Priority Data

Sep. 8, 1993 [KR] Rep. of Korea ............ 93-18040

[51] Int. Cl.$^6$ .................... G01N 27/40; G01N 27/07
[52] U.S. Cl. .................... 324/698; 324/441; 324/446; 324/450; 324/553; 324/693
[58] Field of Search .................... 324/439, 441, 324/444, 446, 450, 551, 553, 693, 698, 713, 715, 718, 726

[56] References Cited

U.S. PATENT DOCUMENTS

| | | | |
|---|---|---|---|
| 3,037,164 | 5/1962 | Doble et al. | 324/553 |
| 4,646,000 | 2/1987 | Wills | 324/444 X |
| 4,849,687 | 7/1989 | Sims et al. | 324/698 X |
| 5,089,780 | 2/1992 | Megerle | 324/448 |
| 5,175,502 | 12/1992 | Rodabaugh et al. | 324/439 |
| 5,262,732 | 11/1993 | Dickert et al. | 324/553 X |
| 5,272,444 | 12/1993 | Cox | 324/698 |

*Primary Examiner*—Kenneth A. Wieder
*Assistant Examiner*—Glenn W. Brown
*Attorney, Agent, or Firm*—Flynn, Thiel, Boutell & Tanis

[57] ABSTRACT

A degradation level of transformer insulating oil can be checked by measuring leakage current of a sensor for measuring the degradation level of the insulating oil, in which DC power is applied to two electrodes of the sensor in the insulating oil for the transformer. In general, free carbons or nonsolute conductive particles are produced in the transformer insulating oil when used over long periods in the power transformer. The porous ceramic of the sensor for measuring degradation level of the insulating oil receives in the pores thereof the conductive impurity particles, and a conductive circuit is formed. Thus, this measurement for degradation level of insulating oil is based on the electric change states for the formation of the conductive circuit. Accordingly, by forming such structures, a method and apparatus for measuring degradation level of insulating oil by measuring leakage current of the sensor are provided. The degradation sensor can be used to measure the degradation level of insulating oil but also can be used to check the overload condition of a pole transformer. The potential level between the electrodes and occurring between the degradation sensors form a constantly rated load which can be measured by conversion into current.

8 Claims, 7 Drawing Sheets

METHOD FOR MEASURING DEGRADATION LEVEL OF TRANSFORMER INSULATING OIL IN USE, AND APPARATUS FOR CARRYING OUT THE METHOD

FIELD OF THE INVENTION

The present invention relates to diagnosing the variation due to aging of insulating oil in an electric apparatus and also abnormal phenomena in the interior of a power transformer using the insulating oil in advance. In order to understand the aging state of the electric apparatus at the first stage, some activities will be done to measure conductivity of the insulating oil to detect the degrading degree thereof, on-line at a remote site or on the spot, depending on the principle of electrical conductive phenomenon of the sensor inserted into the insulating oil. Thus, a detecting target is the particles of conductive impurity, and consequently a measuring method is to detect the small current in μA flowing through a sensor, and as a result the present invention relates to a method and apparatus for measuring a degradation degree of the insulating oil.

BACKGROUND OF THE INVENTION

In a conventional method of measuring a degradation degree of the aging insulating oil in an electric apparatus, sampled materials which have been used for a long time are tested generally by a method of analyzing acid value, applying a breakdown voltage and analyzing a resulting gas at the laboratory, without testing them immediately on the spot, and therefore it has a problem of delay since it is not on the spot testing, as well as a problem in accuracy of the tested value. Produced materials from the aging insulating oil of the electric apparatus generally consist of the gas and the particles of impurity.

Accordingly, a gas analyzing test developed at present and hydrogen gas detection are kinds of measuring methods for the amount of the produced gas. In the analyzing method of the gas produced in the insulating oil of the electric apparatus, the gas ingredient is analyzed by the varied amount of resistance generated between both ends of the electrodes when the gas particles pass through a gas barrier contacted with the porous electrodes.

Therefore, the problems occurring in gas analyzing methods are a great variation of the tested value as well as low reliability of the test result in accordance with the environmental circumstances, because of the nature of the active gas, and also it is a drawback not to be used in general except in big facilities, because the gas analyzing equipments require installation of very expensive chemical accommodations.

In addition, the samples to be tested are taken on the spot in analyzing acid value and applying breakdown voltage, and thereby there is a fear of penetration by air and moisture and due to the above sensor there are lots of problems such as error occurrence of the tested value, low reliability of the tested result by testing in exposure of the air, and the limited apparatuses to be tested.

SUMMARY OF THE INVENTION

In solving the above problems by the present invention, a sensor connected with a DC voltage source in the insulating oil will measure its leakage current through which the degradation degree of the insulating oil will be known. Free carbon or nonsolute conductive particles are produced in the insulating oil due to superheating and penetration of air or moisture when the insulating oil in the elective apparatus is operated for a long period, and further, nonsolute conductive impurity particles in the insulating oil are liable to travel sensitively to the variation of the temperature in the transformer tank, and thus the testing sensor for degradation of the insulating oil forms a conductive circuit in the insulating oil throughout such surrounding conductive particles.

A measuring object of the degradation of the insulating oil is to measure the leakage current flowing through the sensor by regarding such phenomena as a regular changeable state.

Though hydrocarbon as a main component of the insulating oil will generally not be oxidized, an oxidation reaction takes place slowly at the beginning. However, oxidation speed is increased after a certain period, when it starts contact with oxygen moisture or surrounding environment. This is the reason some materials will be produced similar to a catalyzer to expedite oxidation, which is so-called auto-oxidation, as follows:

1. $RH \rightarrow R°$ (Chain reaction start)
2. $R° + O \rightarrow ROO°$ ⎤ (Chain reaction propagation)
3. $ROO° + RH \rightarrow ROOH + R°$ ⎦
4. $R° + R° \rightarrow RR$ ⎤ (Chain reaction termination)
5. $ROO° + R° \rightarrow ROOR$ ⎦

In the foregoing formulas, RH designates a hydrocarbon compound and R° designates a free group.

As shown in formula 1, in a reaction of hydrocarbon a hydrogen (RH) is removed and a free group (R°) connected to the reaction of formula 3 is created. Adding an oxygen in the reaction of formula 3 produces a free group (R°), and then the reaction of formula 2 repeats.

Formulas 4 and 5 designate chain reaction termination and hydroperoxide (ROOH) commences the reaction of formula 6, as follows:

6. $ROOH \longrightarrow RO° + O°H \xrightarrow{RH}$ $ROH + R° + O°H$ (Chain branching)

The degraded materials produced in the oxidation reaction of a hydrocarbon compound in formulas 1, 2, 3, and 6 are divided into the solute products and the nonsolute products, and the solute impurity particles are peroxide (R—OOR), alcohol (ROH), aldehyde (ROHO), ketone (RCO—R), organic acid (R—COOH), acid anhydride $$\begin{matrix} R-CO \\ R'-CO \end{matrix} \Big] O,$$

organic peroxide (ROOH), ester (R—COO—R'), metallic soap ((RCOO) nM) (M means metal atoms), etc., and nonsolute impurity particles include asphaltic sludge, soap sludge and carbon sludge, etc.

The asphaltic sludge educed and precipitated in the heating source area of the transformer will hinder the cooling action of the insulating oil.

The soap sludge produced by the oxidation of the insulating oil and also produced by combination with the metal transformer material eluted into the insulating oil from organic acid and insulating varnish will include a great deal of moisture, and further the following carbon sludge and gaseous material will be produced when the insulating oil is resolved by the discharge of sparking:

7. $C_2H_6 \rightarrow CH_4 + C + H_2$
8. $C_3H_6 \rightarrow C_2H_4 + C + H_2$ $C_2H_6$ shown in formula 7 is ethane, which is a hydrocarbon of the paraffine series, and C of free group remains after producing methane ($CH_4$) and hydrogen ($H_2$) in superheating, and also $C_3H_6$ shown in formula 8 is cyclopropine which is a hydrocarbon of the naphthene group and C of free carbon remains after producing ethylene ($C_2H_4$) and hydrogen ($H_2$) in electric sparking. On observing the electrical characteristics of the free carbon, it is a conductive material having 0.16 Å in radius of the charged particle, 0.0019Ω Cm in resistance ratio and 0.5 Å/cm² in current density.

BRIEF DESCRIPTION OF THE DRAWINGS

The method for measuring degradation level of transformer insulating oil in use and the apparatus thereof according to the present invention will be described in detail below with reference to embodiments shown in the accompanying drawings, in which.

DETAILED DESCRIPTION

Figure 1:
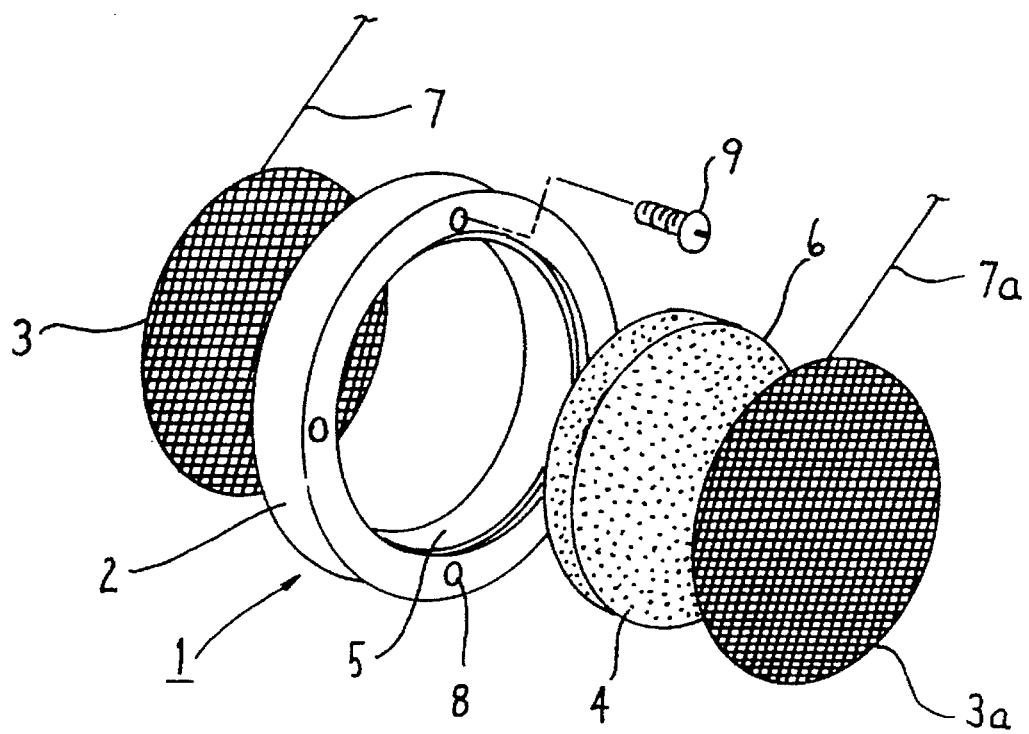
FIG. 1 is an exploded perspective view of a sensor for measuring the degradation level of transformer insulating oil according to the present invention.
Figure 2:
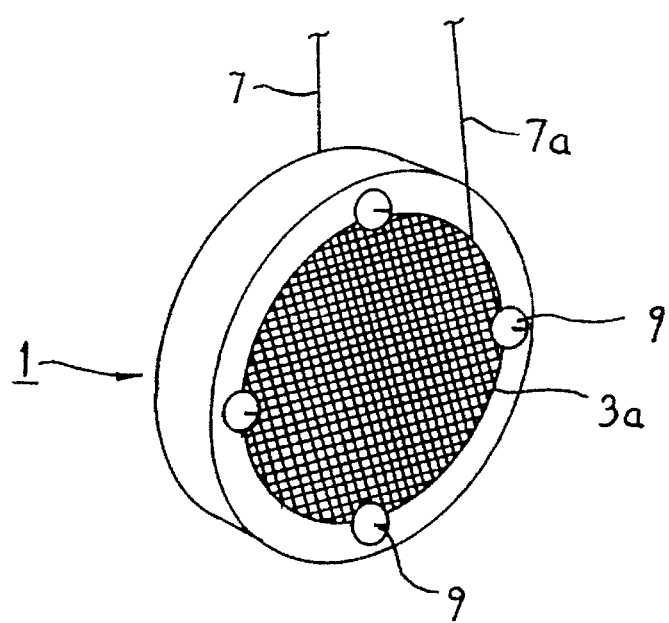
FIG. 2 is a perspective view of the sensor FIG. 1 in an assembled configuration.

FIGS. 1 and 2 are perspective diagrams of the sensor to measure the degradation of the insulating oil in the present invention, the sensor 1 including a base ring 2 to support the sensor, two circular electrodes 3 and 3a, a porous material 4, and insulating bolts 9 to hold the circular electrodes 3 and 3a in place.

The base ring 2 of the sensor 1 is made as a ring type in the center, but it should have good electrical resistance and mechanical strength.

The porous material 4 can be two kinds of material, such as porous ceramic and porous glass, with pores of 70–300 μm in size, and will absorb the conductive particles of the various impurities produced by variation over the elapse of a year.

The mesh size of the circular electrodes 3 and 3a is about 1 mm×1 mm, and the quality of material using stainless steel is preferably etched by plating to last for a long period of time, and also adhesion between the base ring 2 of the sensor 1 and the circular electrodes 3 and 3a is fixed tightly with the insulating bolt 9.

The sensor for measuring the degradation of the insulating oil not only can adsorb the specific material produced in the degrading insulating oil, but can last in it for a long time, and therefore is preferable to withstand oxidation of the insulating oil.

Figure 3A:
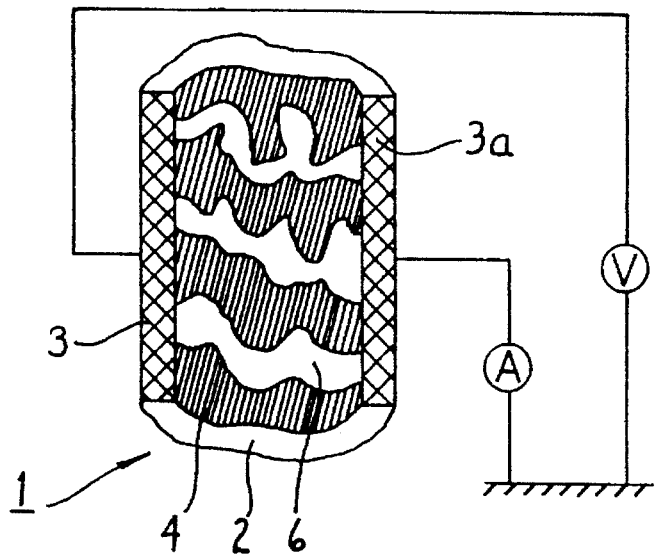
FIG. 3(A) and FIG. 3(B) are electrode circuit diagrams which include the sensor of FIG. 1.
Figure 3B:
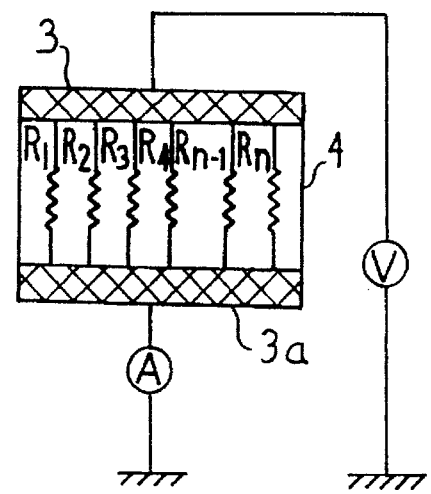

By using the electrical conductivity between the two circular electrodes 3 and 3a with mechanical adherence of the adsorptive material and physical adsorption, the accumulated value of resistance between the electrodes will be revealed depending on the changed amount of the leakage current by applying the predetermined voltage to form the electrode circuit as shown in FIG. 3 (A) and FIG. 3 (B).

When the insulating oil is degraded, the solute and the nonsolute material will be produced, and the conductive particles among such impurity are changed to a mechanical adhesive state by penetrating into the pores of the porous part of the sensor after adsorbing thereon.

When the sensor for measuring the degradation of the insulating oil indicates an electrical conductive state, it will be considered as an element of the conductive ingredient, and the current value of the ammeter A will be changed by applying the predetermined voltage V between the two circular electrodes 3 and 3a of the sensor in the degrading insulating oil.

FIGS. 1 and 2 show the outside view of the sensor and the varied amount of the current can be measured by applying the predetermined voltage between the two circular electrodes 3 and 3a of the sensor 1 in the degrading insulating oil.

Figure 4A:
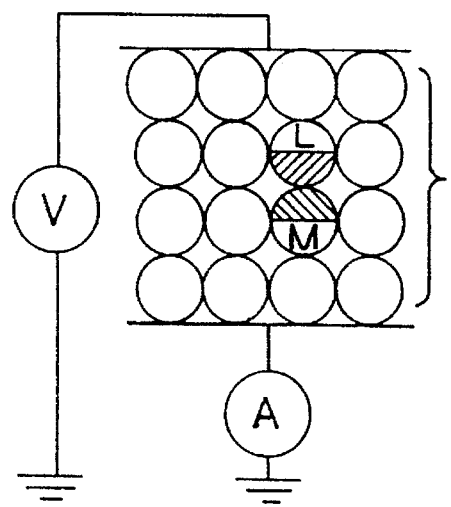
FIG. 4(A) and FIG. 4(B) are model circuit diagrams which explain an ideal adsorption layer.
Figure 4B:
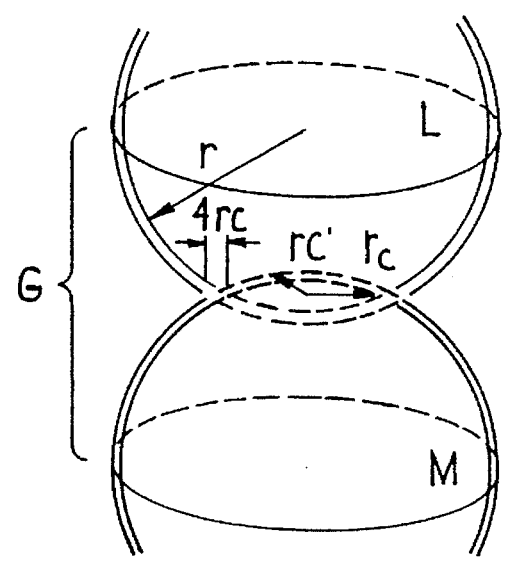

FIG. 4(A) and FIG. 4(B) show the model circuit of the adsorptive layer to calculate the conductivity generated at the adsorptive layer, and also show the sectional condition having the conductivity G between two neighboring layers (parallel sections L and M). Conductivity $\sigma_1$ relating to L and M has an element of conductivity G, and is constituted by series and parallel connections, and also is shown as the following formula since connection is made ½r in series and $1/(2r)^2$ in parallel:

$$\sigma_1 = G \frac{1/(2r)^2}{1/2r} \ [\Omega^{-1}/cm] \qquad a$$

where conductivity G is attained by parallel connection of particle leakage resistance RF and particle self resistance Rc between L and M.

The particle self resistance can be indicated as the sum of the contact resistance generated at the contact point and the oxide film resistance existing at the contact surface, and the contact resistance RS is as follows:

$$Rs = \frac{1}{2rc'} \cdot \frac{1}{\sigma_s} \ [\Omega] \qquad b$$

where $\sigma_s$ is particle self conductivity [$\Omega^{-1}$/cm], rc' is the effective radius (rc'=rc+Δrc) of the contact surface, and the oxide film existing in the contact surface, that is, the resistance of the adsorptive molecule layer, is shown as the following:

$$Rb = \frac{\rho_b}{\pi \cdot rc'^2} \ [\Omega] \qquad c$$

Accordingly, the equation for Rc=Rs+Rb is as follows:

$$Rc = \frac{1}{2rc' \cdot \sigma_s} \cdot \frac{\rho_b}{\pi rc'^2} \qquad d$$

provided that rc', in contact part for lower humidity, is the value in case the capillary condensation of the water molecule is neglected and is increased as much as Arc in case of adsorption of the high polymers in high humidity.

Next, the surface leakage Rf is calculated as the following by considering conductivity of the particle surface as σf:

$$Rf = \frac{\ln(2r/rc')}{\pi \sigma f}$$ e

Therefore, conductivity of the ideal absorption layer is as follows:

$$f = \frac{rc'/r}{1 + (2\sigma_s \rho_p/\pi rc')} + \frac{\pi/2r}{\ln(2r/rc')} \cdot \sigma f [\Omega^{-1}/cm]$$ f provided it is understood that the constituting parameters are r, rc', σs, rf, and σb.

When the f formula is applied to the sensor 1 for measuring the degradation of the insulating oil, it is clear that the conductivity becomes smaller as the charging rate r becomes larger, that is, conductivity $\sigma_1$ becomes less as the pore size becomes smaller.

When rc' is the effective radius of the contact surface, conductivity $\sigma_1$ is larger when the impurity particles that penetrate into the pores 6 of the porous material 4 of the sensor 1 are large as well as in increase of the amount. The conductivity magnitude between two electrodes 3 and 3A is decided, when impurity particles stick in the adsorptive area (pores) between the two electrodes per unit length of the sensor 1.

Although square adsorptive material is used in formula f, its characteristics can be compensated even in the adsorptive material by bringing in the compensated value, in case an irregular and porous material 4 is used.

The substrate (or base ring) of the sensor 1 for measuring of degradation of the insulating oil has not only strong electric insulating resistance, but also significant mechanical strength, and thus it has the following characteristics. When the porous ceramics are utilized for the porous material 4, the material characteristics are as follows:

| | | | |
|---|---|---|---|
| physical properties | Alumina content | % | 96 |
| | absorption rate | % | <0.1 |
| | specific gravity | | 3.0–4.0 |
| mechanical characteristics | hardness | Moh's | 9.0 |
| | | Rockwell HRA | 87 |
| | | KNOOP GPa | 11.1 |
| | compressive strength | kg/cm$^2$ | >2500 |
| | bending characteristics | kg/cm$^2$ | >800 |
| thermal characteristics | safety using temperature in continuous heating | °C. | 1600 |
| | thermal coefficient of expansion | × 10/°C. | 7.2 |
| | thermal conductivity | Cal/cm sec C | 0.05 |
| electric characteristics | cubic resistivity | cm | >10$^4$ |
| | dielectric breakdown voltage | KV/mm | <10 |
| | dielectric constant | 1 MHz 25° C. | 9.6 |
| | dielectric volume rate | 1 MHz tan δ | 0.0003 |

When the porous ceramics are used for the porous material 4, the material characteristics are as follows:
The material: $Al_2O_3$ above 80%
Thermal coefficient of expansion: $6.5–8.5 \times 10^{-6}$/°C.
Specific Gravity: 0.75–0.85
pore rate: 75–85%
pore rate: $V_3/V_1+V_2+V_3 \times 100(\%)$ $V_1$: Volume of ceramic materials
$V_2$: Volume of pore part
$V_3$: Open pore It is preferable to use the porous glass of $SiO_2$ (above 75%) as the porous material 4, and the material of the two circular electrodes (3 and 3A) is made with stainless steel, or with stainless steel etched by plating, having 1 mm×1 mm as the size of the mesh.

In working by the mesh, the surface should be very smooth by etching with an electric beam and the connection between the lead wire 7 and circular electrodes 3 and 3A will be tightly fixed by the insulating bolt 9.

The material of the bolt 9 will be used by FRP having a strong heat-resistance property, or plastics, and also it should not have a relaxative effect or decomposing action. The sensor 1 for measuring the degradation of the insulating oil will be installed at the inside of a power transformer or pole transformer at the time of manufacturing thereof, and the lead wire 7 will be connected to a connecting terminal which is provided at the proper position on the outer wall of the transformer 10. Therefore, it is desirable that the device for measuring a leakage current of the sensor 1 will be manufactured as a portable type or as a remote supervising type to measure the degrading degree of transformer oil.

Thus, at the same time the sensor 1 will have an acid-proof and durable property due to it being installed in the insulating oil.

The porous material 4 having the proper size pore is inserted into the supporting hole 5 of the sensor in supporting plate 2, and the circular electrodes 3 and 3A on both ends will be fixed by the insulating bolt 9 to the bolt hole 8 of the sensor supporting plate 2 described above, and also the lead wires 7 and 7a will be attached to the terminal 11 installed at the outer wall of the transformer 10.

An electric circuit is constituted by the conductive impurity particles passed through the porous part of the sensor 1 for measuring degradation of the insulating oil as described above. That is, the amount of the conductive impurity particles will be checked by measuring the varied value of the current with ammeter A, and also the charge in elapse of a time will be understood by the electric amount of the absorbed insulating oil, when a certain voltage is applied to both electrodes 3 and 3A of the sensor 1.

Figure 5:
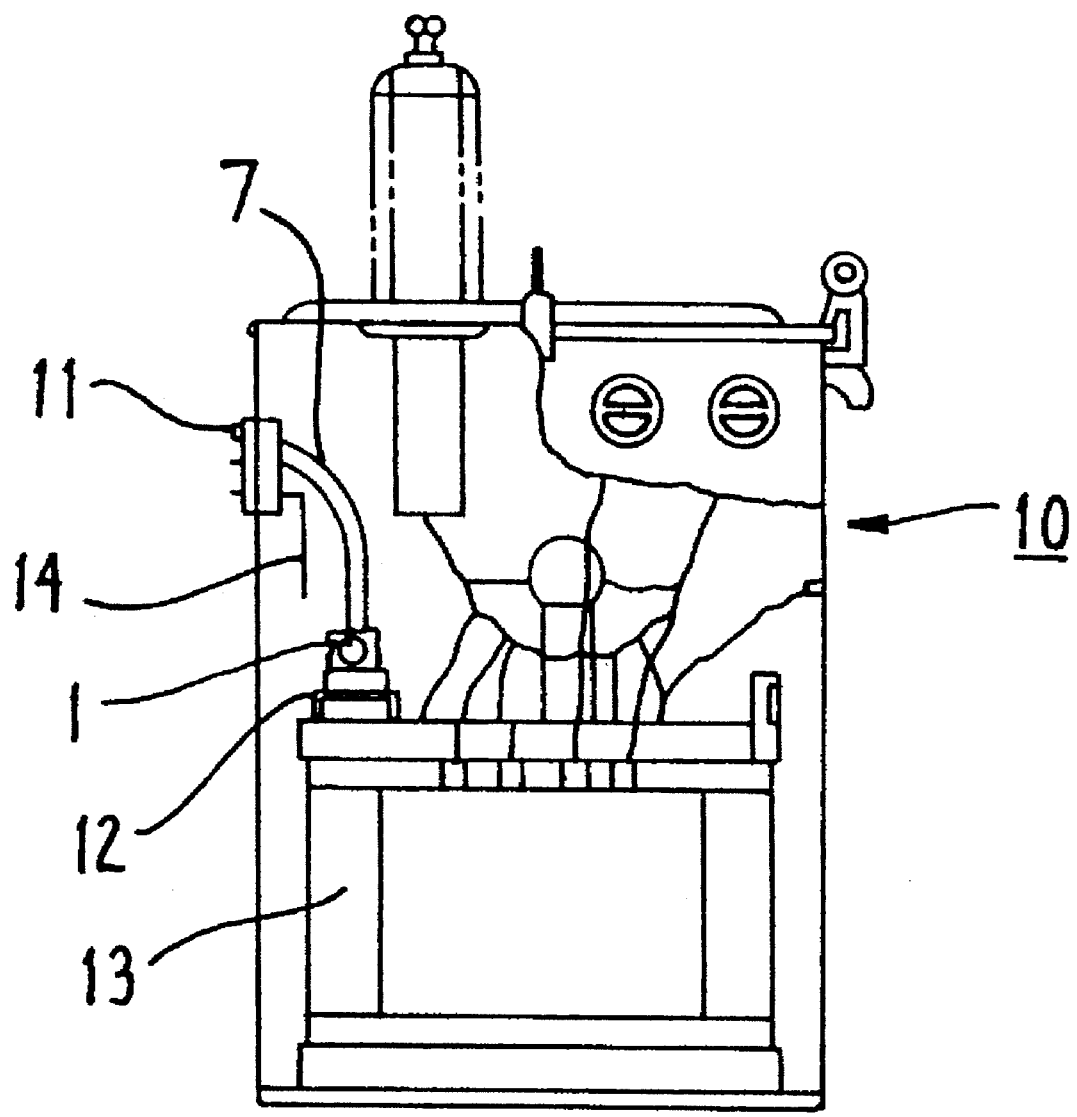
FIG. 5 is a diagrammatic sectional view of the sensor according to the present invention installed in an electric apparatus.

FIG. 5 shows the state-diagram of the pole transformer 10 in use, presently showing the sensor 1 installed on the core supporting material 12 by simply connecting it to the supporting frame 13, and in the connecting method the porous material 4 of the sensor 1 will be opened so that it may thoroughly be contacted with the insulating oil, and also it is necessary for only the sensor supporting plate or ring 2 to be adhered to the supporting frame 13.

The circular electrodes 3 and 3A will be installed in the transformer 10 to keep the insulating distance of the withstand-voltage, and even the lead wire 7 will be fixed by inserting it in the insulating pole to keep the insulating distance of the withstand-voltage.

The compensating temperature sensor 14 will be manufactured to have the combined functions of measuring temperature, and also it will be installed near to the porous material 4 of the sensor 1 for measuring the degradation of the insulating oil as is possible by keeping the insulating distance of the withstand-voltage.

The terminal connector 11 consisting of two terminals of the sensor 1 and a terminal of the compensating temperature sensor 14 will be installed at the outside wall of the transformer 10, and the lead wires 7 and 7a will be connected from the inside of the transformer 10 to the outer wall thereof to measure the sensing current at the outside by hermetically completely sealing-up the terminal so as not to permit an outflow of the insulating oil.

Figure 6:
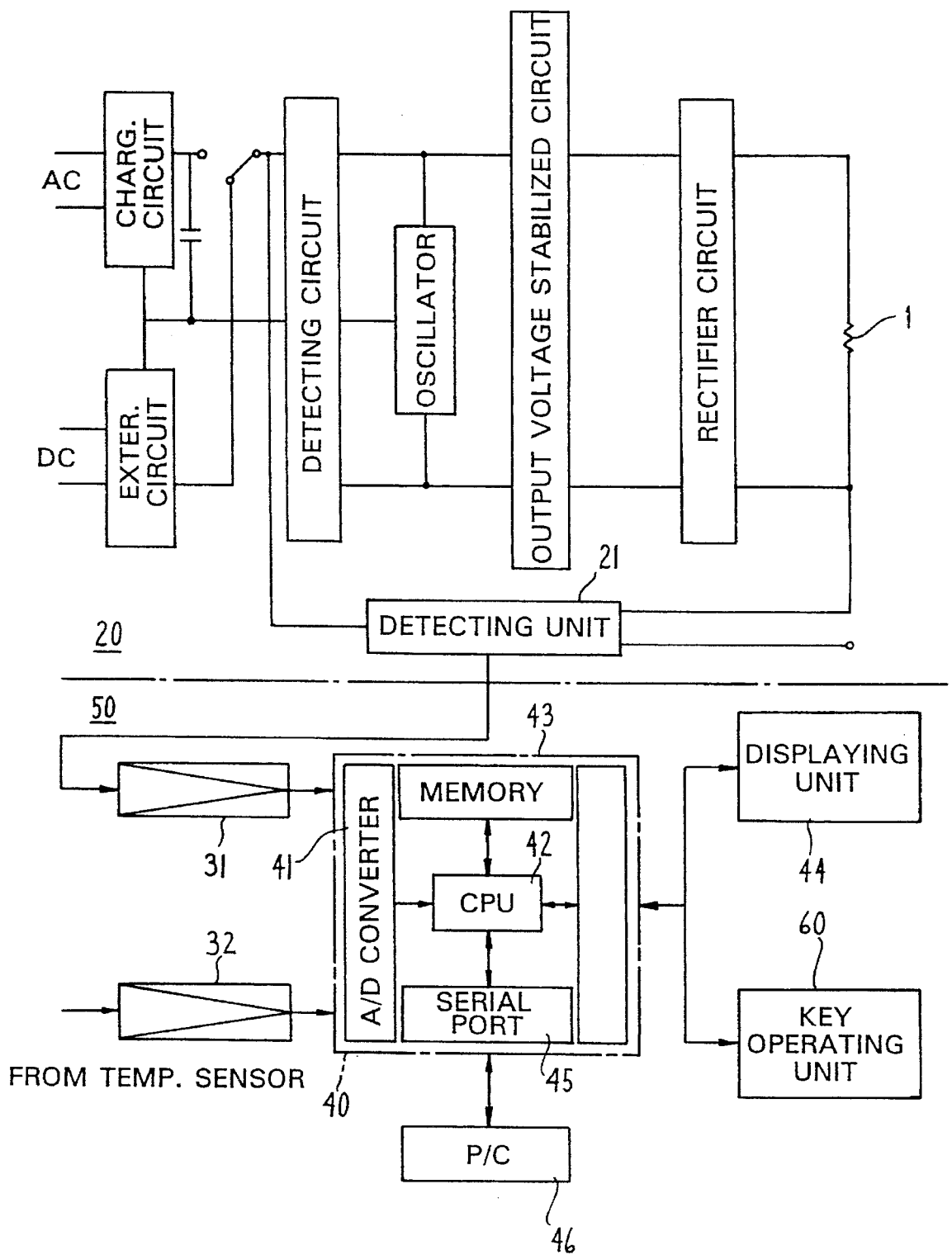
FIG. 6 is an overall circuit diagram of a measuring device according to the present invention which includes the sensor.

Accordingly, the detecting circuit as shown in FIG. 6 is used as the measuring device for measuring the output signals of the sensor 1 and the sensor 14, as described above.

Namely, the DC high voltage generating unit 20 will measure the leakage current by applying the DC voltage to the sensor 1 for measuring the degradation of the insulating oil.

After the output signals of the DC high voltage generating unit 20 and the output signal of the compensating temperature sensor 14 in the transformer are amplified by the amplifier 31 and 32 and are inputted to the microprocessor unit 40, the signals are compared with the predetermined reference value in accordance with the temperature characteristics and will be calculated to store in the memory and to display.

Figure 7:
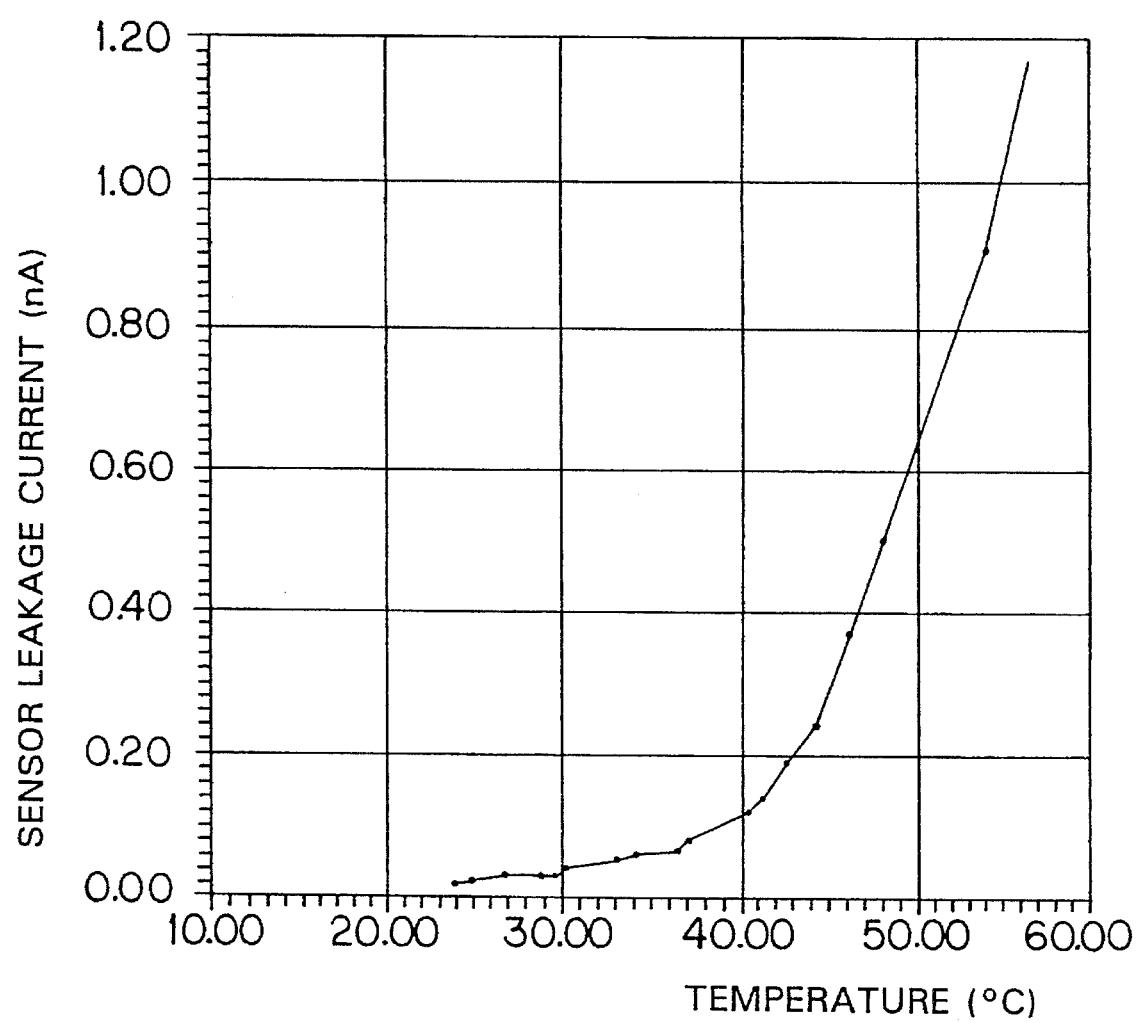
FIG. 7 is a graph showing the temperature characteristics of the sensor for measuring the degradation level of transformer insulating oil according to the present invention.

Thus, when the amplified current and temperature values are inputted to the microprocessor unit 40, the microprocessor unit 40 of the compensating temperature circuit 50 will compare them with the temperature characteristic curve of the sensor 1 of the degrading insulating oil, shown in FIG. 7.

The function of such comparison is performed by the program stored in the RAM of the microprocessor, and thus the calculated value which is the measured value reduced from the reference value in accordance with the temperature characteristics is digitally displayed in the displaying unit 44.

Key operating unit 60 has a function to store and transmit the calculated value as described above.

PORT unit 45 to PC 46 is a transmitting device to analyze and process generally the data measured on the spot, and only the terminals are installed externally.

The hardware of the present measuring device includes the DC high voltage generating unit 20 and the compensating temperature circuit 50. Indicating method of the numerals is performed in a digital mode at the DC high voltage generating unit 20. The compensating temperature circuit 50 includes microprocessor 40, temperature amplifier 32 and current amplifier 31, and the source voltage of the DC high voltage generating unit 20 will generate the voltage in the range of 1–10 by the variable stepping switch.

The signals of the leakage current and the temperature will be amplified by the amplifiers with respective characteristics and are inputted to the A/D connector 40 for CPU 42, and then the CPU receives the signals and transmits the standard data to P/C unit 46 through the serial port 45 and also it is designed to perform the graphic operation.

Figure 8:
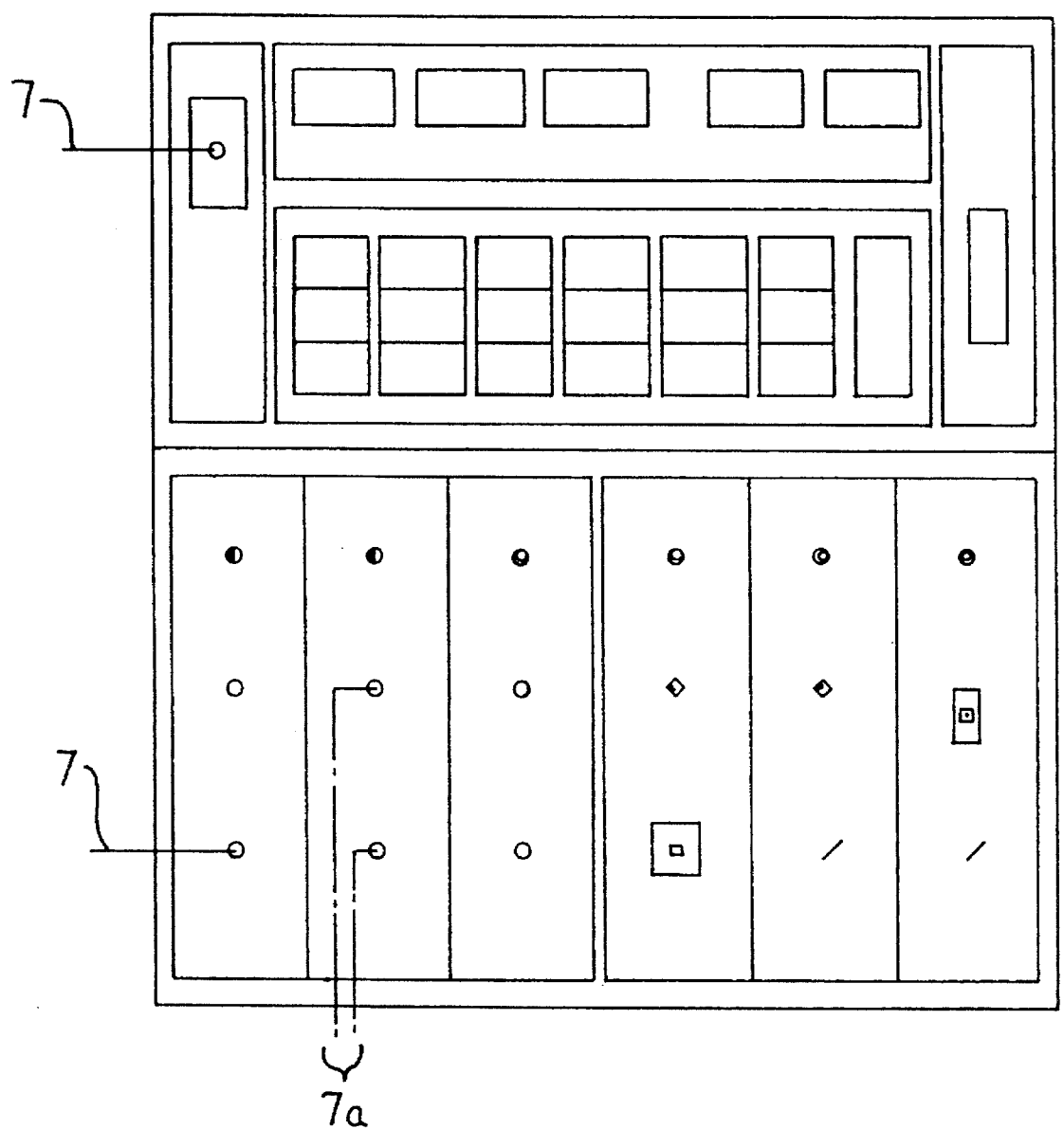
FIG. 8 is a view for explaining use of the measuring device according to the present invention.

Since the relation between the sensor 1 and the measuring device is as shown in FIG. 8, it is always possible to measure the leakage current of the sensor as a portable device by pulling out the terminal connector from the measuring device.

Also, it will be possible to input the data by program in accordance with the temperature characteristics curve (FIG. 7) of the sensor measured in new insulating oil, because the sensor of the insulating oil has its own temperature characteristics.

The lead wire for measuring the temperature will be CC or T/C type, and the leakage current can be measured at the time of measuring the sensor for measuring the degradation of the insulating oil in accordance with the temperature.

The leakage current value is inputted by A/D conversion after the amplifier, and the microprocessor will measure the present degrading degree of the insulating oil by comparing two values.

By receiving the input signal of the leakage current corresponding to each temperature at the time of measuring the degradation of the insulating oil, the microprocessor will indicate on the measuring device the reduced value of the leakage current in accordance with each temperature.

In order to solve the problems of the common ground between the DC high voltage generating unit and the microprocessor unit in measuring leakage current, the isolation amplifier is used, and the degree of amplification is shown as follows.

$$V_o = V_{signal} \times \left(1 + \frac{R_F}{R_G}\right)$$

$$R_F \geq 20K\Omega$$

In the two foregoing formulas, $V_o$ means degree of amplification, $V_{signal}$ the voltage of the signal, RF the resistance of feedback, and RG the input resistance.

The microprocessor unit to be used in the present measuring device has fundamentally a random access memory (RAM) function to store data temporarily, a read only memory (ROM) function to store the software permanently, and a communication PC (personal computer) to transmit the data, and also has a key-pad function to handle all the input and output signals.

As described above, the programs to analyze, store and transmit the data are stored in the microprocessor circuit, and then the programs are compared with the compensating temperature value already stored in the microprocessor, and thereafter the calculated data will be indicated on the measuring device or be transmitted.

In the remote supervisory system for the sensor for measuring the degradation of the insulating oil, it is possible to promptly measure the degradation of the insulating oil of the pole transformer or the power transformer at the control for the distribution line through the distribution line carrier system or the communication line by installing a modem on the outer case of the transformer.

Figure 9:
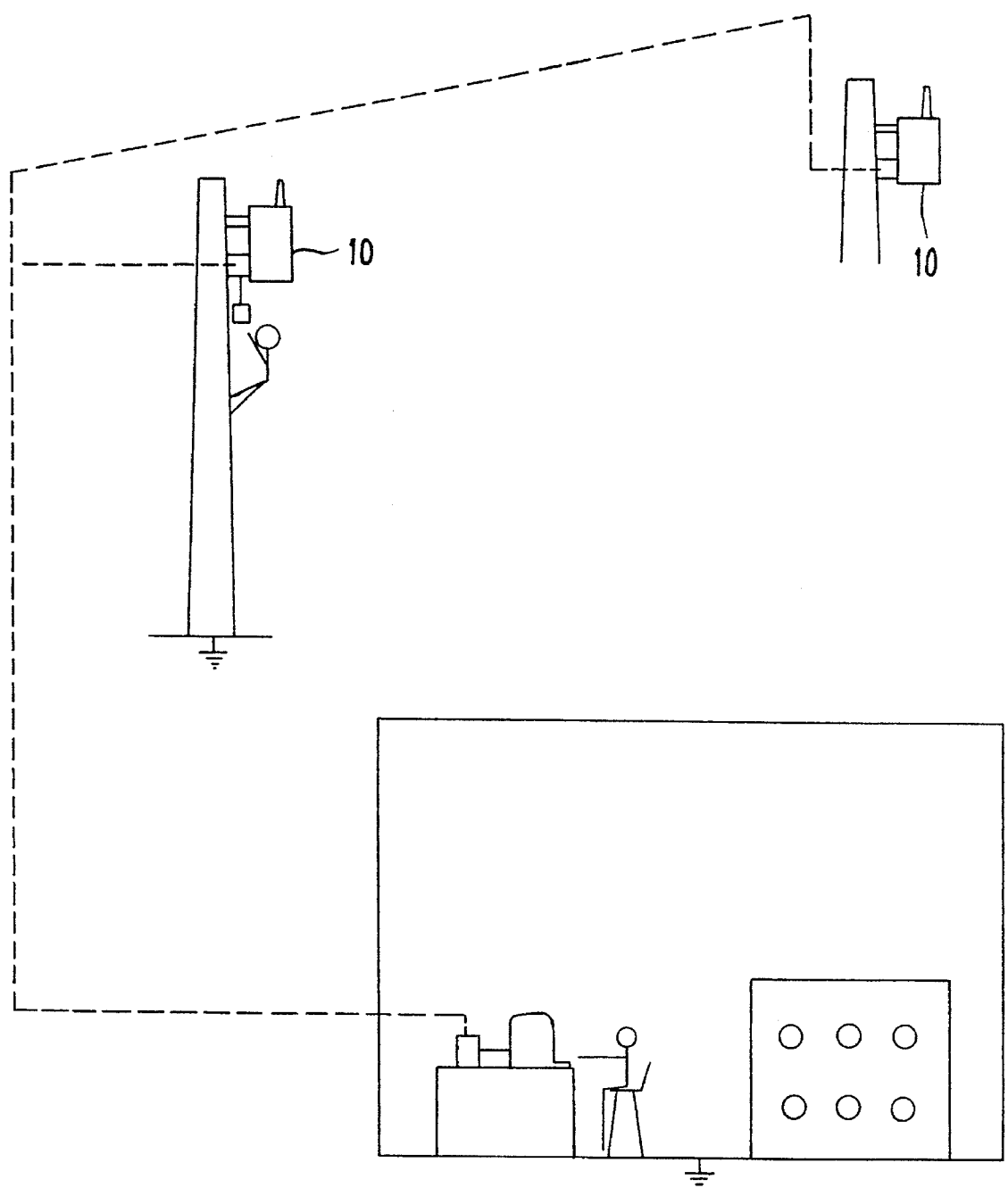
FIG. 9 is a diagrammatic view for explaining a remote measuring state for a transformer by use of the measuring device according to the invention.

The remote measuring system is exemplified in FIG. 9, and thus the present measuring device has some important characteristics, such as the fact that measurements with the sensor are made sensitive to temperature by attaching the compensating temperature circuit, and the fact that the system can measure the sensor at the remote supervisory system by attaching the computer function of storing and transmitting the data via a transmission terminal.

A measuring method and a measuring principle for overload states of the transformer will be described below.

The transformer is a stopping device whereat the potential level is transferred depending on the number of turns in the coil to produce an electromagnetic force when the current flows through the coils. Accordingly, on the top of the iron core and surroundings thereof, the electromagnetic force is always in the induced state. The degradation sensor, according to the invention, comprises electrodes maintaining a predetermined gap on the top of the iron core for the transformer, and the electromagnetic force between the electrodes is induced by the following principle.

In the degradation sensor, the capacitance C between two planar electrodes is produced according to the following equation:

$C = \epsilon_o\, A/d$ wherein $\epsilon_o$ = permeability

A = electrode area d = distance between the electrodes

The potential level difference $(V_1 - V_2)$ taking place between both electrodes and the electrostatic energy produced at this time is calculated as follows:

$$W = \frac{1}{2} C(V_1 - V_2)^2 = \frac{\epsilon_o A(V_1 - V_2)^2}{2d}$$

wherein

W=electrostatic energy

Accordingly, the potential level difference between both electrodes has as the following:

$$V = V_1 - V_2 = \sqrt{\frac{2dW}{\epsilon_o A}}$$

As described in the above equations, the potential level difference between both electrodes in the degradation sensor is proportional with the electrostatic energy, and is related to the materials for the degradation sensor.

Further, the electrostatic energy W is directly influenced by resistance loss in the direct resistance of the windings in the transformer, eddy current loss within the conductors, and stray loss caused by leaking flux from the transformer parts, except the winding. The stray loss is related to design and manufacture of the transformer product, and the loss brought about by measuring the potential level difference V for the degradation sensor. The quality of the transformer can be checked and the overload states of the transformer also can be checked before the insulating oil in the transformer is degraded.

In the measuring method, the existing, conventional, testers can be used and the display panel, whereat the A/D convertor for measuring very small voltage is attached to the lead wire terminal 7a of the tester for measuring the degradation level of the insulating oil, can be used.

In the circuit for transferring load current into the potential level difference, the A/C convertor is used and on the panel the load current is to be displayed, the top part of the panel additionally having a transfer switch for facilitating a measuring of the potential level difference.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A method for measuring a degradation level of transformer oil in use, comprising the steps of:

placing a degradation sensor into a volume of transformer insulating oil for measuring a degradation level of the transformer insulating oil, said degradation sensor including a base ring pierced by a supporting hole in the central part, a porous ceramic material provided with pores and disposed in the supporting hole, and two circular electrodes on both ring sides, the electrodes being held on the base ring by insulating bolts engaging threaded holes in the base ring, the porous ceramic material being adapted to allow impurity conductive particles to pass into the pores, with a lead wire on one of the electrodes being connected to and extending between a terminal on a terminal box of a transformer;

placing a temperature sensor near the degradation sensor and measuring the temperature of the transformer oil near the degradation sensor, said temperature sensor including a lead wire connected to and extending between a further terminal on the terminal box of the transformer;

applying a constant DC voltage from a DC high voltage producing unit to the circular electrodes and utilizing a detecting unit for detecting the existence of current conversion values; and providing circuits which output current signals to the detecting unit of the DC high voltage producing unit, said current signals being amplified and inputted to an A/D converter and thence to a CPU of a microprocessor unit whereat the signals and a current temperature signal from the temperature sensor are compared with existing data stored in the microprocessor unit, stored in the memory of the microprocessor unit, displayed on a display unit and transmitted to a personal computer through a serial port on the microprocessor unit.

2. The method for measuring a degradation level of transformer insulating oil of claim 1, including the step of carrying out remote measurement for the degradation level of transformer insulating oil using the serial port of the microprocessor unit.

3. The method for measuring a degradation level of transformer insulating oil of claim 1, wherein the physical characteristics and electrical properties of the degradation sensor are used in order to measure the degradation level of transformer oil in the field as well as check overload states of the pole transformer in live line.

4. The method for measuring a degradation level of transformer insulating oil of claim 1, wherein the quality of the transformer is checked by measuring the potential level across the degradation sensor before deterioration of the transformer oil occurs.

5. An apparatus for measuring a degradation level of transformer oil in use comprising:

a degradation sensor for measuring a degradation level of transformer insulating oil, including a base ring pierced by a supporting hole in the central part, a porous ceramic material provided with pores and disposed in the supporting hole, and two circular electrodes on both ring sides, the electrodes being held on the base ring by insulating bolts engaging threaded holes in the base ring, the porous ceramic material being adapted to allow impurity conductive particles to pass into the pores with a lead wire on one of the electrodes being connected to and extending between a terminal on a terminal box of a transformer;

a temperature sensor which is disposed near the degradation sensor for measuring the temperature of the transformer oil near the degradation sensor and includes a lead wire connected to and extending between a further terminal on the terminal box of the transformer;

a DC high voltage producing unit which applies constant DC voltage to the circular electrodes and is provided with a detecting unit for detecting the existence of current conversion values; and a circuit which outputs current signals to the detecting unit of the DC high voltage producing unit, said current signals being amplified and inputted to an A/D converter and thence to a CPU of a microprocessor unit whereat the signals and a current temperature signal from the temperature sensor are compared with existing data stored in the microprocessor unit, stored in the memory of the microprocessor unit, displayed on a display unit and transmitted to a personal computer through a serial port on the microprocessor unit.

6. The apparatus for measuring a degradation level of transformer insulating oil of claim 5, including the step of carrying out remote measurement for the degradation level of transformer insulating oil using the serial port of the microprocessor unit.

7. The apparatus for measuring a degradation level of transformer insulating oil of claim 5, wherein the physical characteristics and electrical properties of the degradation sensor are used in order to measure the degradation level of transformer oil in the field as well as check overload states of the pole transformer in live line.

8. The apparatus for measuring a degradation level of transformer insulating oil of claim 5, wherein the quality of the transformer is checked by measuring the potential level across the degradation sensor before deterioration of the transformer oil occurs.

* * * * *